(12) United States Patent
Bevacqua et al.

(10) Patent No.: US 8,673,345 B2
(45) Date of Patent: Mar. 18, 2014

(54) DISSOLVABLE FILM COMPOSITION

(75) Inventors: Andrew J. Bevacqua, E. Setauket, NY (US); Peter J. Lentini, Bellmore, NY (US); Tracy N. Keeler, Fort Salonga, NY (US); Julius R. Zecchino, Closter, NJ (US); Pauline Vassiliou, Franklin Square, NY (US)

(73) Assignee: E-L Management Corp., New York, NY (US)

(*) Notice: Subject to any disclaimer, the term of this patent is extended or adjusted under 35 U.S.C. 154(b) by 269 days.

(21) Appl. No.: 11/968,755

(22) Filed: Jan. 3, 2008

(65) Prior Publication Data

US 2008/0102103 A1    May 1, 2008

Related U.S. Application Data

(63) Continuation of application No. 11/158,153, filed on Jun. 21, 2005, now abandoned.

(60) Provisional application No. 60/581,842, filed on Jun. 22, 2004.

(51) Int. Cl.
*A61K 8/02* (2006.01)
*A61K 36/82* (2006.01)

(52) U.S. Cl.
USPC ............ 424/444; 424/447; 424/401; 424/729

(58) Field of Classification Search
None
See application file for complete search history.

(56) References Cited

U.S. PATENT DOCUMENTS

| | | | |
|---|---|---|---|
| 4,188,373 A | 2/1980 | Krezanoski | |
| 4,990,339 A | 2/1991 | Scholl et al. | |
| 5,466,718 A | 11/1995 | Nakatsu et al. | |
| 5,723,138 A | 3/1998 | Bae et al. | |
| 5,976,565 A | 11/1999 | Fotinos | |
| 6,139,856 A | 10/2000 | Kaminska et al. | |
| 6,248,341 B1 * | 6/2001 | Anderson et al. | 424/401 |
| 6,258,344 B1 * | 7/2001 | Venkateswaran | 424/62 |
| 6,310,255 B1 | 10/2001 | Nagato et al. | |
| 6,497,887 B1 | 12/2002 | Zecchino et al. | |
| 6,517,628 B1 | 2/2003 | Pfaff et al. | |
| 6,565,839 B2 | 5/2003 | de la Poterie et al. | |
| 6,565,865 B2 | 5/2003 | Bekele | |
| 6,592,887 B2 | 7/2003 | Zerbe et al. | |
| 2002/0192287 A1 | 12/2002 | Mooney et al. | |
| 2003/0235606 A1 | 12/2003 | Nussen | |
| 2003/0235630 A1 | 12/2003 | Nussen | |
| 2004/0180077 A1 | 9/2004 | Riker et al. | |

FOREIGN PATENT DOCUMENTS

| | | |
|---|---|---|
| EP | 0 750 905 | 1/1997 |
| JP | 09-216808 | 8/1997 |
| JP | 9278648 | 10/1997 |
| JP | 20011508037 | 6/2001 |
| JP | 2003-073250 | 3/2003 |
| JP | 2005-306871 | 11/2005 |
| KR | 10-2000006163 | 10/2000 |
| WO | WO94/05341 | 3/1994 |
| WO | WO95/05416 | 2/1995 |
| WO | WO98/17251 | 4/1998 |
| WO | WO01/78692 | 10/2001 |
| WO | WO02/092049 | 11/2002 |
| WO | WO03/030882 | 4/2003 |

OTHER PUBLICATIONS

English translation of JP 09-216808-1997.*
http://web.archive.org/web/20030428175409/http://www.freezedry.com/fl_tips.htm—internet archived version from Apr. 28, 2003.*
Flick (Cosmetic Additives: An Industrial Guide. 1991: Noyes Publications: USA, pp. 233-234).*
PCT International Search Report; International Application No. PCT/US05/21739; Completion Date: Feb. 14, 2006; Date of Mailing: Jun. 2, 2006.
PCT Written Opinion of the International Searching Authority, or the Declaration; International Application No. PCT/US05/21739; Completion Date: Feb. 14, 2006; Mailing Date: Jun. 2, 2006.
Westerman, Kaila; What is Glycerin?; www.pioneerthinking.com/glycerin.html; 1997.
Supplementary European Search Report; 05766015.1; Completion Date: Aug. 21, 2009: Date of Mailing: Sep. 3, 2009.

* cited by examiner

*Primary Examiner* — Susan Hoffman
(74) *Attorney, Agent, or Firm* — Julie M. Blackburn

(57) ABSTRACT

A kit and methods for delivering an effective amount of a labile active to the skin are provided. The kit and methods comprise a composition comprising an effective amount of a labile active agent incorporated into a water-soluble polymeric film and an additive composition capable of dissolving the water-soluble polymeric film.

14 Claims, No Drawings

DISSOLVABLE FILM COMPOSITION

Under 35 U.S.C. 120, the following continuation application claims benefit of U.S. Ser. No. 11/158,153, filed Jun. 21, 2005, now abandoned, which claims priority under 35 U.S.C. 119e of U.S. provisional application 60/581,842 filed Jun. 22, 2004.

FIELD OF THE INVENTION

The present invention relates to a dissolvable film composition for application to the skin. In particular, the present invention relates to a dissolvable film composition that provides stable actives for delivery to the skin.

BACKGROUND OF THE INVENTION

A common problem in cosmetic compositions has been the effective delivery of actives to the skin. Since cosmetic compositions often have numerous ingredients to make it cosmetically acceptable, the amount of active is often diluted. Moreover, the presence of other ingredients can impede the amount of active that is actually delivered within the skin. Even if ingredients in the cosmetic compositions do not impede effective delivery of the active to the skin, the active may fail to successfully adhere to the skin to deliver essential actives to the skin.

Moreover, many actives are unstable in cosmetic vehicles. For example, Polyphenone E, the active component of Green Tea, drastically discolors and loses activity when incorporated into an emulsion containing water. Polyphenone E is known to possess potent anti-tyrosinase activity. Skin pigmentation and tanning are related to the amount of melanin in epidermal melanosomes. In the melanosomes, the enzyme tyrosinase oxidizes tyrosine and the resulting intermediate compounds polymerize to form the brown-black melanin pigment. The formation of melanin is believed to be a defensive mechanism in humans which protects their skin from harmful ultraviolet rays. However, the excessive formation of melanin following prolonged sun exposure or due to disorders of epidermal melanin units is responsible for melasma, ephelides, and pigmented cosmetic dermatitis. Although the precise mechanism of excessive melanin formation has not been fully elucidated, the activation of tyrosinase appears to be a significant factor. Thus, the development of chemical agents capable of modulating the enzyme activity of tyrosinase would have considerable value for the control of the above-noted undesirable skin conditions. See U.S. Pat. No. 5,466,718.

Hinokitiol is a bacterial fungicide that is known to have anti-irritant, anti-microbial and skin lightening properties. However, when Hinokitiol is incorporated into an emulsion, the Hinokitiol develops a strong, unpleasant odor and discolors the emulsion to a yellowish-brown color upon storage.

Retinoids constitute a large group of synthetic and naturally occurring compounds related to retinol, the vitamin A alcohol. In mammals, retinoids fulfill essential roles, including maintenance of epithelial cells. However, retinoids are known to be chemically unstable and nearly insoluble in water. Therefore, retinoids are difficult to incorporate into cosmetic compositions.

Other examples include vitamins that are unstable in cosmetic compositions. For example, vitamin C has many skin benefits for the skin, including whitening and stimulating collagen synthesis. As is known in the art, collagen synthesis makes the skin stronger, which helps reduce lines and wrinkles. However, vitamin C is known to be very unstable when exposed to water, oxygen and light and therefore loses its activity and drastically discolors.

Therefore, there continues to be a need for a topical delivery system that is effective in delivering an unstable active to the skin while creating a stable environment for that active.

SUMMARY OF THE INVENTION

The present invention provides a kit and methods for delivering an effective amount of a labile active to the skin, comprising a composition comprising an effective amount of a labile active agent incorporated into a water-soluble polymeric film and an additive composition capable of dissolving the water-soluble polymeric film.

DETAILED DESCRIPTION OF THE INVENTION

The following provides definitions for the terms used in the present invention.

Definitions:

The term "effective amount" means an amount sufficient to cause a cosmetic effect to the skin.

The term "water soluble" means the material is at least 95% soluble in water.

The term "labile active" refers to an active that changes or breaks down from its natural state and/or loses potency or activity when exposed to environmental factors such as air, water, and light as well as cosmetic formulations such as emulsions.

Since cosmetic compositions are often in the form of emulsions, unprotected labile actives are exposed to water, or are provided in packaging that gives little protection against environmental exposure. Therefore, when unprotected labile actives are provided in cosmetic compositions, the desired effect of the actives may be diminished because of degradation of the labile actives. Thus, there is a need to provide a means of not only packaging the actives to avoid lability, but also to deliver the actives in a protected manner.

To this end, the present invention provides a system that delivers an effective amount of a labile active to the skin in a protected manner. In a preferred embodiment, the system comprises a composition comprising an effective amount of a labile active agent incorporated into a water-soluble polymeric film and an additive composition capable of dissolving the water-soluble polymeric film.

The labile active may be any cosmetic ingredient that is subject to environmental degradation, as for example, antioxidants, antiaging agents, whitening agents, UV-protective agents, skin conditioning agents, or combinations thereof. In one embodiment, the actives of the present invention are selected from polyphenol actives. In another embodiment, the labile active is specifically selected from the group of green tea extracts, white tea extracts, red tea extracts, black tea extracts, licorice extracts, phytosphingosine, ethylbisiminomethylguaiacol manganese chloride, white birch extract, hinokitiol, coffee extract, hoelen mushroom extract, ascorbic acid, siegesbeckia, rosemary extract, silymarin, Boswellia extract, ubiquinone, retinoids, resveratrol, potassium cholesterol sulfate, protease enzymes, lipase enzymes, apigenin, vitamin E, grape seed extract, lutein, licochalcone, luteolin, ursolic acid, Centella asiatica extract, ximenynic acid, ferulic acid, amentoflavone, dihydroxyacetone, conjugated linoleate, salicylic acid, 1, 3-Beta Glucan, and triclosan, and combinations thereof. Where extracts are noted above, it will be understood that reference thereto should also encompass any and all labile active components of that extract. A list of labile actives and extracts, as well as the cause of their lability are provided in Table 1 below.

TABLE 1

| Ingredient | Key Issue(s) | Function | Air Light Heat Water Metal |
|---|---|---|---|
| Green Tea Extract and isolates | Stability | Antioxidant | ALHWM |
| Licorice Extract | solubility, stability | Antioxidant, antiinflammatory, lightening | ALHWM |
| Phytosphingosine/Biosine | solubility, formula compatibility | Barrier repair | solubility |
| Ethylbisiminomethylguaiacol Manganese Chloride | Color | Antioxidant | HLA |
| White Birch extract | Solubility | HSP inductor, antiinflammatory | solubility |
| Hinokitiol | odor, stability | Anti tyrosinase, antimicrobial, antiinflammatory | LHM |
| Coffee extract | odor, color | Barrier repair | LH |
| Hoelen Mushroom Extract | solubility, color, odor | Anti-inflammatory | HL |
| Ascorbic Acid/Ascorbyl glucoside | stability, formula compatibility | Antioxidant, whitening, collagen synthesis | ALHWM |
| *Siegesbeckia* | color stability | Anti-collagenase | ALH |
| Rosemary Extract | solubility, color | Antioxidant | ALH |
| Silymarin | solubility, color | Anti-elastase | ALH |
| *Boswellia* Extract | Odor | Anti-inflammatory, stimulates cell regeneration | LAH |
| Ubiquinone | Stability | Antioxidant, cell energy | ALH |
| Retinol | Stability | Cellular differentiation regulator | ALHWM |
| Resveratrol | Color | Antioxidant | ALH |
| Potassium Cholesterol Sulfate | Solubility | Barrier repair | solubility |
| Enzymes (proteases, lipases, etc) | Stability | Exfoliation | ALHWM |
| UVA/UVB absorbers | Solubility, odor (some) | UV attenuation | LHM |
| Apigenin | Color, | Cell protection | L |
| Vitamin E | Color, stability | Antioxidant | LAH |
| Grape Seed Extract | Color, stability | Antiox, anti-elastase/collagenase | ALHM |
| Lutein | Color, stability | Antiox | ALHWM |
| Licochalcone | Color, stabiity | Antiinflammatory, whitening | ALHWM |
| Luteolin | Color, stability | Anti-histamine, anti-collagenase | ALH |
| Ursolic Acid | Solubility | Anti-elastase, ornithine decarboxylase inhibitor | ALHM |
| *Centella Asiatica* Extract | Solubility | Collagen systhesis stimulator | LHM |
| Ximenynic Acid | Stability, color | Antiinflammatory | ALHWM |
| Ferulic Acid | Stability, color, odor, solubility | Antiox, whitening, uva absorber | ALHWM |
| Amentoflavone | Color, solubility | Antiinflammatory | ALH |
| Dihydroxyacetone | Color, odor, formula compatibility | Sunless tanning agent | ALHWM |
| FD&C Blue # 1(Acid Blue) and others | Color, formula compatibility | Dyestuff | ALHM |
| Conjugated linoleate(CLA) | Color, odor, formula compatibility | EFA, lipolysis | ALHW |
| Various Fragrance Components such as essential oils and aromatic oils. | Color, odor, formula compatibility | Organoleptic, aromatheraputic | ALHWM |
| Salicylic Acid and derivatives | Formula compatibility, solubility | Keratolytic, anti-acne | AHWM |
| 1,3-Beta Glucan(1'6'), | Formula compatibility, solubility | Wound healing agent | AHM |
| Triclosan | Formula compatibility, stability | Antibacterial agent | LHM |

The effective amounts of the labile active as used in the methods and kit of the present application will vary depending on the active selected and the cosmetic benefit desired, but ordinarily will be within the range of known active concentrations for the selected material, or in some cases, may be lower because of the greater retained activity. Overall, as a guideline, the ranges will typically be from 0.001% to 5% by weight of the total composition. As an example, in a preferred embodiment, the effective amounts of hinokitiol is from 0.001% to 0.5%, preferably from 0.01 to 0.3% and most preferably from 0.05 to 0.1%. As another example, the effective amounts of antioxidants such as from plant extracts, are from 0.001% to 2%, preferably from 0.01% to 1.5% and most preferably from 0.1% to 1%. It should be noted that the labile actives may be used in combination in the methods and kit of the present invention as long as each active does not interfere with the stability of the other actives. A person of ordinary skill in the art would be capable of identifying such combinations based on information generally available regarding the lability of different actives.

Another component of the methods and kit of the present invention is a water-soluble polymeric film, comprising at least one water-soluble film-forming agent in which the labile active is incorporated. Surprisingly, the water-soluble polymeric film protects the labile active from the factors that contribute to their lability before incorporation. Specifically, the water-soluble polymeric film does not contain any water or water-based ingredient, thereby avoiding the solubility and stability issues encountered when attempting to incorporate the labile active within a typical, water-containing cosmetic medium. The labile active is preferably incorporated into a side of the water-soluble polymeric film that contacts the skin. Upon application of the water-soluble polymeric film to the skin and subsequent dissolution of the film, the labile active is effectively transferred to the skin in a substantially unaltered state to provide the desired cosmetic benefits.

In the preferred embodiment, the water-soluble polymeric film should be inherently tacky or sticky/adhesive such that the film is capable of adhering to the skin upon application of the water-soluble polymeric film to the skin.

Examples of the water-soluble film-forming agents that can produce a tacky, water-soluble polymeric film include but are not limited to collagen derivatives, cellulose derivatives, e.g., nitrocellulose, cellulose ether, carboxymethylcellulose, hydroxymethylcellulose, hydroxypropylcellulose; pullulan, homo- and copolymers of vinyl pyrrolidone, e.g., PVP or PVP/PVA copolymers; homo- or copolymers of vinyl alcohol, such as polyvinyl alcohol, homo- or copolymers of acrylic and/or methacrylic acids, and salts and esters thereof, starches and derivatives thereof, or gums such as xanthan gum, gum arabica, guar gum, carob bean gum, cellulose gum, alginates, vegetable proteins, shellac, crotonic acid polymers, adipic acid polymers or carageenans, and mixtures thereof. In general, methods of making films from these water-soluble film-forming agents are well known in the art.

It should be noted that more than one water-soluble polymeric film-forming agent may be used in combination to form a first layer in which the labile active is incorporated.

In a preferred embodiment, the composition comprises at least two layers of polymeric films. Preferably, a second water-soluble polymeric film is also used to provide physical stability to the final composition, thereby providing more lubrication and spreadability for the adhesive water-soluble polymeric film layer incorporating the labile active. Such a second film should be used in such amounts so as not to interfere with the dissolvability of the composition on the skin. It is preferred that the second water-soluble polymeric film be different from the first water soluble polymeric film containing the active so that two discrete layers may be maintained.

Examples of useful water-soluble film-forming agents for this purpose, include, but are not limited to, polyethylene, high molecular weight polyethylene glycols (PEGs), hydrophilic siloxysilicates, hydrophilic silicone polyacrylates and combinations thereof. It should be noted that more than one water-soluble film-forming agent may be used in combination to form the second layer of water-soluble polymeric film, with the limitation that each of the agents of the second layer must be different from the water-soluble film-forming agent or agents of the first layer to maintain the two distinct layers.

In a preferred embodiment, the water-soluble film-forming agent of the first adhesive film layer is used in an amount of 30% to 90% by weight of the wet composition, preferably from 35% to 75%, and most preferably from 40% to 70%.

In a preferred embodiment, the water-soluble film-forming agent of the second film layer is present in an amount of from 2% to 50% by weight of the wet composition, preferably from 4% to 40%, and most preferably from 6% to 30%.

In the preferred embodiment, the first layer of a water-soluble polymeric film incorporating the labile active is made with a solution for casting films. The solution is made by dissolving a small amount of a water-soluble film forming polymer in water. An effective amount of the labile active ingredient of choice is added directly to the resulting solution. The solution is then mixed to uniformity, and poured, for example, onto a clean ceramic tile plate or other suitable surface, and rolled over the plate until a uniform coating of the solution is achieved. The plate is then either baked in an oven to accelerate the evaporation of the water (if the labile active can tolerate the heat), or it is dried with means known to those of ordinary skill in the art, such as a commercial hand-held hair dryer, or overnight with a fan, to render the solution coating to a film. The method used will depend on the active used and the reactivity of the active to water. For example, films containing those actives that are more water sensitive will be dried immediately, whereas those actives that are water-stable can be dried overnight. The water-soluble polymeric film is dried so that the film is essentially dry and contains no more than 2% water, preferably no more than between 0.1% to 1%.

When making a two layer composition, the second layer of water-soluble polymeric film is adjacently adhered to a side opposite the active in the first water-soluble polymeric film by methods known to those skilled in the art, such that the second polymeric film does not interfere with the active. Specifically, both the first layer of water-soluble polymeric film and second layer of water-soluble polymeric film are dried, as described above. Thereafter, the second layer of water-soluble polymeric film is adhered by methods to those skilled in the art for creating polymeric layers, such as by roller laminating the second layer of water-soluble polymeric film upon the first layer of water-soluble polymeric film so that the second layer is adjacently adhered to the first layer, thereby creating two distinct layers. The second layer of water-soluble polymeric film may be roller laminated onto the first layer of water-soluble polymeric film by methods known in the art.

The resultant water-soluble polymeric film composition is then cut to size. In a preferred embodiment, the film composition will be further packaged, for example in a plastic or foil packet, in the form of a patch, or in other protective enclosures. In the user's hands, the patch is applied to skin, where it is re-dissolved by means described hereinbelow. An example of the resultant first layer of water-soluble polymeric film composition is provided in Example 1 below. An example of the resultant two layer film composition is provided in Example 2 below.

The foregoing paragraphs describe the basic elements of the composition comprising a labile active incorporated in to a water-soluble polymeric film. However, it may be desirable to incorporate other components into the film.

In one embodiment, the inventive water-soluble polymeric film composition may further comprise a plasticizer incorporated therein to provide additional lubrication and spread for the water-soluble film-forming polymer. The plasticizer may be any material which does not interfere with the labile active, as would be known to those skilled in the art. If a plasticizer is used, the labile active or actives may be incorporated directly into the plasticizer before the plasticizer and water-soluble film forming polymer are dried using the methods described hereinabove.

A nonlimiting list of exemplary materials which may act as plasticizers for the film forming polymers of the present invention includes diisobutyl adipate, acetyl tri-n-butyl titrate, di(2-ethyl hexyl) azelate, 2-ethyl hexyl diphenyl phosphate, diisoctyl isophthalate, isooctyl benzyl phthalate, butyl stearate, tri-2-ethyl hexyl trimellitate, N-octyl neopentanoate, diisostearyl malate, colloidal fumed silica (such as Cab-O—Sil®, sold by Cabot Corp.) and most perfume materials. Preferably, the plasticizer is a polyol such as 1,3 butylene glycol, because of its known properties of providing plasticizing effects at minimal concentrations.

The plasticizer, if used, is present in an amount from 0.01% to 20%, preferably from 0.1% to 10%, and most preferably from 0.15% to 5% of the wet composition.

Those skilled in the art will readily recognize that the foregoing components represent the preferred elements of the inventive film, but that other optional elements that constitute the cosmetic/therapeutic effect may be included. These optional elements are selected so as not to disturb and in some cases, will preferably enhance the stability of the labile active. Such optional components include but are not limited to, stabilizers, preservatives, surfactants, emulsifiers, dyes and other non-labile actives.

As an additional component of the system for delivering labile actives, a wetting solution or additive solution is utilized. Since the labile actives are relatively unstable when exposed to factors such as water or air, it is recommended that such labile actives be sheltered from such factors until the actives are transferred into the skin. However, in order to function on the skin, the water-soluble polymeric film is preferably wetted with an additive composition that is a wetting solution or activator. The additive composition is provided separately from the water-soluble polymeric film so that the composition does not contribute to the instability of the labile active prior to delivery of the active to the skin. The additive composition is used to wet the water-soluble polymeric film so that when the labile active contacts the skin, it is transferred to the skin as the water-soluble polymeric film dissolves. The labile active is maintained, as part of the film, in a relatively stable state until the actual moment of application to the user's skin.

The additive composition may be as simple as ordinary water or water miscible ingredients or components such as polyols, depending on the relative water solubility of the water-soluble polymeric film used and the nature of the additional components in the inventive composition. The additive composition is preferably capable of wetting the film carrying the labile active upon application of the film to the skin to release the labile active therein.

The additive composition may beneficially comprise any number of additives and actives as long as such additives and actives are not of a nature or used in an amount to interfere with the aqueous nature of the additive composition, including, but not limited to such ingredient classes as described in The CTFA Cosmetic Ingredient Handbook, Tenth Edition (2004), including abrasives, absorbents, aesthetic components such as fragrances, pigments, colorings/colorants, essential oils, skin sensates, astringents, etc., anti-acne agents, anti-caking agents, antifoaming agents, antimicrobial, antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition, opacifying agents, pH adjusters, propellants, reducing agents, sequestrants, skin bleaching and lightening agents, skin-conditioning agents (e.g., moisturizers, emollients or humectants), skin soothing and/or healing agents, skin treating agents, thickeners, and vitamins and derivatives thereof. Although categorized by benefit, it should be noted that the actives useful herein can in some instances provide more than one benefit or operate via more than one mode of action. Therefore, classifications herein are made for the sake of convenience and are not intended to limit the active to that particular application or applications listed.

More specific examples of useful additional components in the additive composition include retinoids such as retinol, and esters, acids, and aldehydes thereof; ascorbic acid, and esters and metal salts thereof, tocopherol and esters and amide derivatives thereof; shark cartilage; milk proteins; alpha- or beta-hydroxy acids; DHEA and derivatives thereof; topical cardiovascular agents; clotrimazole, ketoconazole, miconozole, griseofulvin, hydroxyzine, diphenhydramine, pramoxine, lidocaine, procaine, mepivacaine, monobenzone, erythromycin, tetracycline, clindamycin, meclocyline, hydroquinone, minocycline, naproxen, ibuprofen, theophylline, cromolyn, albuterol, hydrocortisone, hydrocortisone 21-acetate, hydrocortisone 17-valerate, hydrocortisone 17-butyrate, betamethasone valerate, betamethasone dipropionate, triaminolone acetonide, fluocinonide, clobetasol, proprionate, benzoyl peroxide, crotamiton, propranol, promethazine, and mixtures thereof. Particularly preferred embodiments of the present methods and kits include skin care patches useful as whitening products, incorporating actives such as hinokitiol.

It should be noted that the ingredients in the additive composition may overlap those identified as labile actives in the water-soluble film forming polymer. However, the actives in the additive composition are used in the manner commonly used in cosmetic formulations and not to provide the surprisingly effective cosmetic benefit provided by delivering the labile active in a relatively better protected state, as is found in the present inventive system.

Kit

The elements useful for carrying out the present method, comprising the two elements of the film comprising a labile active and the additive composition, may be provided as separate elements. For example, the user may apply the film to the skin, and thereafter dissolve the film by application of simple tap water, or by the application of a separately obtained additive cosmetic composition, such as a water-based emulsion or toner, that is capable of dissolving the film. In a preferred embodiment, however, for the convenience of the end user, the elements are provided as a kit, i.e., a unit package containing both the water-soluble film containing the labile active, combined with a separate container containing the additive composition. The unit package may be a box, tin, cardboard cylinder, or shrink wrap that conveniently holds the components together. In one embodiment, the package may be adapted to further stabilize the components by reducing exposure to environmental factors, i.e., it may be airtight or darkened to avoid exposure to light. The elements provided in the package may also be presented in different forms. For example, the film may be provided in a convenient dispenser, or may be individually packaged in plastic, foil, paper, cellophane, or glassine packets or envelopes in the form of a patch. The additive composition, which will typically be of a fluid nature, may be packaged in a glass or plastic bottle (e.g., squeeze or pour bottle, or aerosol or non-aerosol pump), or glass or plastic jar, or any other suitable container for holding a fluid composition.

Preferred Method of Use

The present inventive methods and kit can be used to yield numerous benefits. The water-soluble polymeric film incorporating a labile active may be applied to the skin and rewetted using the additive composition, thereby transferring the labile active to the skin in a stable form. The methods and/or kit therefore serve as an excellent means of delivering a labile active to the skin. The film carrying the labile active may be made in any shape or size to accommodate the treatment needed. Therefore, the appropriately shaped film could be used for spot treatment or as a mask for a larger area of treatment. A specific example is the use of the methods and/or kit for delivering actives that provide a whitening effect. Rather than application of a whitening composition to an entire skin surface, a film patch can deliver whitening agents directly to age spots or discolored areas. For this purpose, whitening agents such as hinokitiol, kojic acid, hydroquinone, ascorbic acid, magnesium ascorbyl phosphate, and ascorbyl glucoside may be incorporated into the film and wetted using the additive composition to transfer the whitening agent to the areas of the skin where whitening is desired.

The methods and/or kit may be used on various parts of the skin such as corners of the eyes, along the upper lips, and other areas in need of an intense direct treatment, for example, with an anti-aging or anti-wrinkle treatment. For example, a preferred use of the present inventive methods and/or kit is for spot wrinkle treatment. A patch containing one or more anti-wrinkle actives can be applied directly to the area to be treated, for example, on crow's feet, under eyes, around the lips, neck area, deep furrows on the forehead, and brow area. Examples of labile, anti-wrinkle or anti-aging actives include retinoids, vitamin C, 2-hydroxyalkanoic acids, prostaglandins, ceramides and their derivatives.

A nonlimiting list of possible actives and corresponding benefits are provided in Table 1 hereinabove. In the case of inclusion of more than one labile active into the kit of the present invention, the active(s) will be incorporated in an amount sufficient to deliver the known effective dosage of each particular labile active.

The following examples further illustrate the invention, but the invention is not limited thereto.

EXAMPLE 1

A water-soluble polymeric film of the present invention incorporating a labile active may be formulated as provided below in Table 2. Table 2 provides the weight percentages of the elements of the composition prior to drying the film.

TABLE 2

| Ingredient | CTFA name | Percent |
| --- | --- | --- |
| Methocel K4M Premium | Cellulose Ether | 2.00% |
| 1,3-Butylene Glycol | 1,3 Butylene Glycol | 2.00% |
| Green Tea Polyphenol | Polyphenol | 0.5% |
| Deionized Water | Purified Water | Q/s |

EXAMPLE 2

The composition shown below in Table 3 provides an example of an alternative embodiment of the present invention providing a first layer of adhesive water-soluble polymeric films incorporating labile actives and a second layer of water-soluble polymeric film adjacently adhered to the first layer. The patch is intended primarily for whitening of the skin. The weight percentages of the elements indicate the amount in the final, dried composition.

An example of an activator or additive composition is provided in Table 4 below. The compositions in Table 3 and Table 4 combined provide the system and kit of the present invention.

TABLE 3

| INVENTIVE POLYMERIC FILM COMPOSITION | | | |
| --- | --- | --- | --- |
| COMPONENT | FUNCTION | CHEMICAL NAME | PERCENTAGE |
| ADHESIVE WATER SOLUBLE FILM FORMING LAYER CONTAINING LABILE ACTIVES | | | |
| PVP | Adhesive film layer | Polyvinylpyrrolidone | 47.558900 |
| POLYVINYL ALCOHOL | Adhesive film layer | Polyvinyl alcohol | 4.750000 |
| WATER (AQUA PURIFICATA) PURIFIED | | Water | 1.797700 |
| *CAMELLIA SINENSIS* LEAF EXTRACT | Labile active | GREEN TEA EXTRACT | 1.050300 |
| HINOKITIOL | Labile active | Hinokitiol | 0.100000 |
| DISODIUM EDTA | Chelating agent | | 0.040000 |
| SODIUM SULFITE | Stabilizer | | 0.040000 |
| BUTYLENE GLYCOL | Plasticizer | | 0.035000 |
| PROPYLENE GLYCOL | Plasticizer | | 0.025000 |
| *CUCUMIS SATIVUS* FRUIT EXTRACT | Labile active | CUCUMBER FRUIT EXTRACT | 0.010000 |
| *PYRUS MALUS* FRUIT EXTRACT | Labile active | APPLE FRUIT EXTRACT | 0.010000 |
| *SCUTELLARIA BAICALENSIS* EXTRACT | Labile active | | 0.0020000 |
| BLUE 1 (CI 42090) | Labile active | | 0.001100 |
| SECOND FILM FORMING LAYER | | | |
| PEG-9 | Second film-forming polymer | Polyethylene glycol | 41.350000 |
| CETETH-10 | Surfactant | | 3.040000 |
| GLYCERIN | Plasticizer | Glycerin | 0.150000 |

TABLE 4

ADDITIVE COMPOSITION

| COMPONENT | CHEMICAL NAME | PERCENTAGE |
|---|---|---|
| RED TOURMALINE | TOURMALINE | 0.0050 |
| METHYL PARABEN NF | METHYL PARABEN | 0.3000 |
| DISODIUM EDTA/TRILON BD | DISODIUM EDTA | 0.1000 |
| CAFFEINE POWDER | CAFFEINE | 0.2000 |
| SUCROSE, ULTRA PURE | SUCROSE | 2.0000 |
| SODIUM HYALURONATE HMW | SODIUM HYALURONATE | 0.0900 |
| AS-G POWDER | ASCORBYL GLUCOSIDE | 2.0000 |
| CAUSTIC SODA 30% | WATER/SODIUM HYDROXIDE | 0.7500 |
| TWEEN 40 | POLYSORBATE 40 | 2.5000 |
| GLYCYRRHETINIC ACID (18-BETA) | GLYCYRRHETINIC ACID | 0.0500 |
| SILICONE 200 (100 CTS.) | DIMETHICONE | 5.0000 |
| DOW CORNING 245 FLUID | CYCLOPENTASILOXANE | 15.0000 |
| MYRISTYL ALCOHOL M-43 | MYRISTYL ALCOHOL | 1.2500 |
| EMERESSENCE 1160 (ROSE ETHER) | PHENOXYETHANOL | 0.7000 |
| ALPHA BISABOLOL NATURAL | BISABOLOL | 0.1000 |
| GRASNOW-HP | HYDROLYZED RICE EXTRACT | 0.1000 |
| INFLAN-ATM | GENTIAN EXTRACT | 0.1000 |
| YEAST EXTRACT AE | YEAST EXTRACT | 1.0000 |
| N-ACETYL-D-GLUCOSAMINE | ACETYL GLUCOSAMINE | 0.1000 |
| ACTIPHYTE OF THYME BG50P | BUTYLENE GLYCOL/WATER/*THYMUS VULGARIS* (THYME) EXTRACT | 0.1000 |
| *GINKGO* EXTRACT HS 2464 G/A | *GINKO BILOBA* LEAF EXTRACT | 0.0100 |
| HYDROLITE 5, 2/016020 | PENTYLENE GLYCOL | 2.0000 |
| SANGUIIN BR-25 | BURNET (*SANGUISORBA OFFICINALIS*) EXTRACT | 0.0100 |
| ABSCENTS DEODORIZING POWDER 2000 | ZEOLITE | 0.2500 |
| SKIN LIGHTENING BLEND 3ELN | *MORUS NIGRA* (MULBERRY) ROOT EXTRACT/*SCUTELLARIA BAICALENSIS* EXTRACT/*VITIS VINIFERA* (GRAPE EXTRACT) | 1.0000 |
| SEPIGEL 305 | POLYACRYLAMIDE/C13-14 ISOPARAFFIN/LAURETH-7 | 3.0000 |
| FRAGRANCE RL-1797 | FRAGRANCE | 0.1650 |
| SEPIGEL 305 | | 0.5000 |
| Deionized Water | Purified water | Q/s |

EXAMPLE 3

This example illustrates the use and performance of the system of the present invention.

This is a controlled study which consists of two months of product use. The test site is the face of selected female panelists. The women are instructed to refrain from using any treatment products on the test site during the test period except for the test products provided. Skin evaluations are carried out before treatment (baseline), and two, four, and eight weeks during the course of treatment.

The women are instructed to apply 2 patches of the composition described in Table 3 above, to each side of the face once a day in the morning. The patch is pressed firmly onto the skin for 15 to 30 seconds. The tab is gently peeled back, leaving the blue active film on the face. A dab of additive composition described in Table 4 hereinabove is applied to each patch, and blended into the skin for 10 to 15 rotations until the film dissolves and is absorbed into the skin. On the day of testing, the women do not apply the product for at least 12 hours before measurements are taken. Product use is monitored by a daily diary as well as assessment of remaining package content at the end of the study.

Skin Tone Study:

At the outset of the study, a particular area to measure skin tone on the cheeks of each panelist is marked. The images of that specific portion of the face are obtained using a fiber optic microscope (Scalar, Vacaville, Calif.) at a resolution of 640× 320 (approximately 1 sq. cm.)

Three images are recorded from each cheek. The same area is photographed at each time point following the initial visit. The stored RGB images are digitized and analyzed using an image analysis program, Optimas 6.51. The standard deviation of the average Grey value of each of the three color channels is determined. This is a measure of the amount of variation in the picture in terms of color. If a product has been effective in evening skin color there will be a decrease in variation and a concomitant decrease in the variance of the Grey value.

Age Spots Study:

At the outset of the study, a particular area demonstrating age spots on the cheeks or hand of each panelist is marked. The images of that specific portion of the face or hand are obtained using a fiber optic microscope (Hi-Scope) at a magnification of 20×. Three age spots are chosen per panelist. The same area is photographed at each time point following the initial visit. The stored RGB images are digitized and analyzed using an image analysis program, Optimas 6.51. The stored RGB images are digitized and analyzed to determine the average Grey value (i.e. density) and area of the corresponding age spot. If a product is effective in diminishing the appearance of age spots, an increase in Grey Value (density) and a decrease in spot area will occur.

Skin Whitening Study:

Skin whitening is assessed and documented with close up photography. Photos of the right and left facial cheeks are taken with a Nikon M3 digital camera. Panelists heads are placed in a head rest to insure reproducibility of positioning. The camera is positioned two feet from the panelist at an F stop of 32. A crossed polarized lens is used to remove all glare from the photographs. Photos are evaluated via an image analysis program, Optimas 6.51, comparing before and after product use. Whitening is analyzed by determining the average Grey value of the three color channels (RGB) in each photograph. If the product has been effective in whitening skin there will be an increase in the Grey value.

As can be seen in Table 5 below, the kit of the present invention significantly (p<0.05) improved skin tone, as compared to the baseline measurement, by an average of 46%, reduced the appearance of age spots by an average of 44%, and improved skin whitening by an average of 36% after 8 weeks of product use as compared to pre-treatment.

TABLE 5

| | Percent Improvement | | |
|---|---|---|---|
| Claim: | 2 weeks | 4 weeks | 8 weeks |
| Skin Tone | 32% | 41% | 46% |
| Age Spots | 25% | 38% | 44% |
| Whitening | 21% | 31% | 36% |

EXAMPLE 4

The same study as in Example 3 above, using the compositions of Tables 3 and 4 above is repeated with a new panel composed of 17 different women.

As can be see in Table 6 below, the system of the present invention improved skin tone compared to the baseline evaluation, by 49%, reduction in appearance of age spots by 47% and skin whitening by 40%.

TABLE 6

| | Percent Improvement | | |
|---|---|---|---|
| Claim: | 2 weeks | 4 weeks | 8 weeks |
| Skin Tone | 39% | 47% | 49% |
| Age Spots | 29% | 42% | 47% |
| Whitening | 30% | 37% | 40% |

What is claimed is:

1. A method for treating age spots on skin for improvement comprising applying to the individual age spots for a period of two to eight weeks a patch comprised of a dried water soluble cellulose ether polymeric film impregnated with at least one skin lightening agent effective to lighten age spots, which is normally labile in one or more of air, light, heat, water, or metal; and at least one plasticizer selected from polyethylene glycol, butylene glycol, glycerin, propylene glycol, or mixtures thereof; wherein the activity of the labile active is maintained in the cellulose ether polymeric film; followed by application of at least one water based additive composition to the film in an amount sufficient to cause the film to completely dissolve and deposit the lightening agent in its active form onto the age spots and improve the appearance of the age spots 25% to 47% over baseline.

2. The method of claim 1 wherein the skin lightening agent is a polyphenol.

3. The method of claim 1 wherein the skin lightening agent is a tea extract.

4. The method of claim 1 wherein the skin lightening agent is green tea extract.

5. The method of claim 1 wherein the water soluble cellulose ether polymer is operable to produce a tacky film when applied to skin.

6. The method of claim 1 wherein the water soluble cellulose ether polymer is nitrocellulose, carboxymethylethylcellulose, hydroxymethylcellulose, hydroxypropylcellulose, or mixtures thereof.

7. The method of claim 1 wherein the water based additive composition comprises silicone.

8. The method of claim 7 wherein the water based additive composition comprises dimethicone, cyclomethicone, or mixtures thereof 9. The method of claim 1 wherein the patch is stored in an air tight packet.

10. The method of claim 1 wherein the additive composition is stored in a bottle.

11. The method of claim 1 wherein the patch is applied to the age spots to be treated at once per day.

12. The method of claim 1 wherein the patch is applied to the age spots once per day in the morning.

13. The method of claim 1 which consists essentially of applying to the individual age spots for a period of two to eight weeks a patch comprised of a dried water soluble cellulose ether polymeric film impregnated with at least one skin lightening agent effective to lighten age spots, which is normally labile in one or more of air, light, heat, water, or metal and at least one plasticizer selected from polyethylene glycol, butylene glycol, glycerin, propylene glycol, or mixtures thereof; wherein the activity of the labile active is maintained in the cellulose ether polymeric film; followed by application of at least one water based additive composition to the film in an amount sufficient to cause the film to completely dissolve and deposit the lightening agent in its active form onto the age spots and improves the appearance of the age spots 25% to 47% over baseline.

14. The method of claim 13 wherein the patches are applied to one or more individual age spots once per day in the morning.

* * * * *